United States Patent
Marcadis et al.

[11] Patent Number: 5,158,565
[45] Date of Patent: Oct. 27, 1992

[54] LOCALIZATION NEEDLE ASSEMBLY

[75] Inventors: Stuart J. Marcadis, Portage, Ind.
Garey L. McLellan, Jacksonville, Fla.

[73] Assignee: DLP, Inc., Grand Rapids, Mich.

[21] Appl. No.: 594,940

[22] Filed: Oct. 10, 1990

[51] Int. Cl.$^5$ .............................................. A61B 17/34
[52] U.S. Cl. ..................................... 606/185; 128/754
[58] Field of Search ................ 606/185; 128/751, 752, 128/753, 754; 604/164, 165, 264

[56] References Cited

U.S. PATENT DOCUMENTS

| | | | |
|---|---|---|---|
| 4,362,156 | 12/1982 | Feller, Jr. et al. | 604/165 |
| 4,517,965 | 5/1985 | Ellison | 128/754 |
| 4,713,057 | 12/1987 | Huttner et al. | 604/264 |
| 4,774,948 | 10/1988 | Markham | 606/185 |
| 4,790,329 | 12/1988 | Simon | 128/754 |
| 4,799,495 | 1/1989 | Hawkins et al. | 128/754 |
| 4,931,059 | 6/1990 | Markham | 606/185 |
| 4,953,558 | 9/1990 | Akerfeldt | 128/754 |
| 4,986,279 | 1/1991 | O'Neill | 128/754 |

*Primary Examiner*—C. Fred Rosenbaum
*Assistant Examiner*—William W. Lewis
*Attorney, Agent, or Firm*—Barnes, Kisselle, Raisch, Choate, Whittemore & Hulbert

[57] ABSTRACT

A localization needle having an inner and outer needle, the outer needle having a window at the distal end and the inner needle having a barb to project out of the window upon relative axial movement of the needles. A first hub on the inner needle has axially spaced recesses to retain and locate a second hub on the outer needle. The first hub is expandable to allow motion of the second hub from a proximal to a distal position. A manually operable flexible oval within the first hub is used to expand the first hub to allow the relative movement of the second hub.

5 Claims, 2 Drawing Sheets

U.S. Patent    Oct. 27, 1992    Sheet 1 of 2    5,158,565
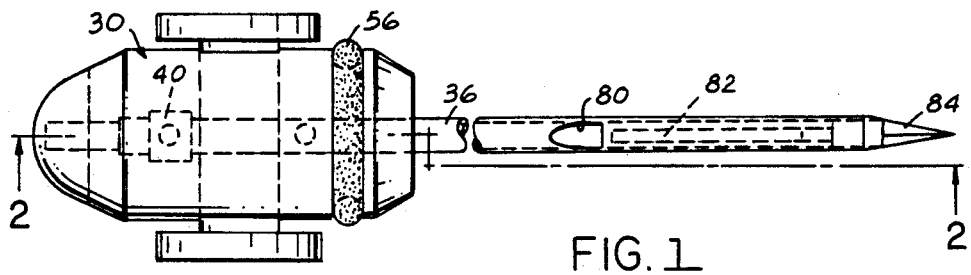
FIG. 1
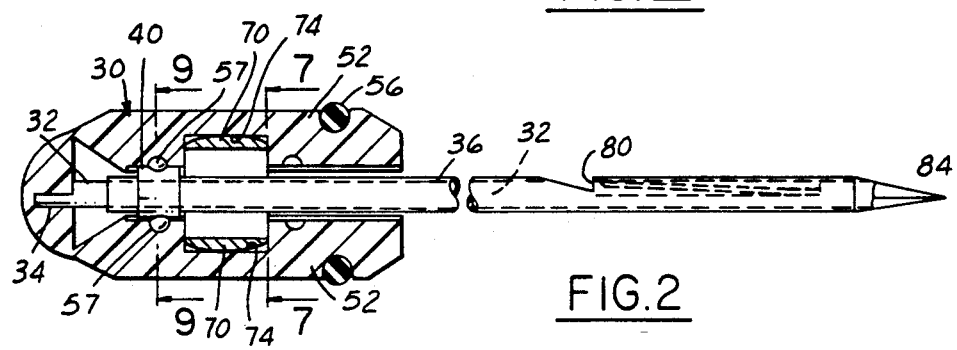
FIG. 2
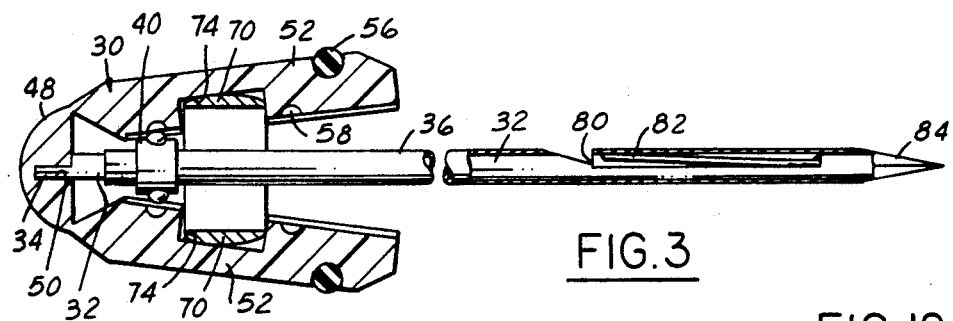
FIG. 3
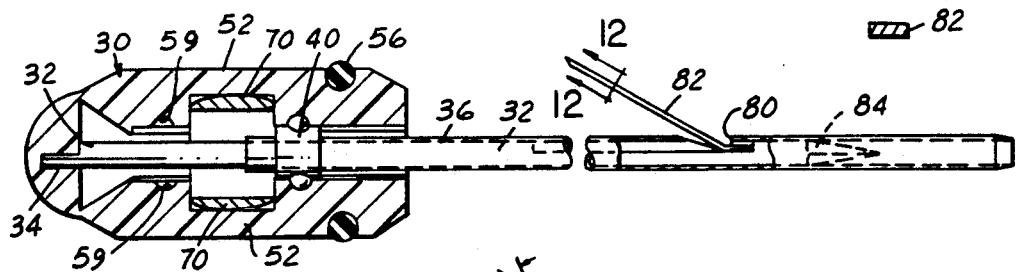
FIG. 4
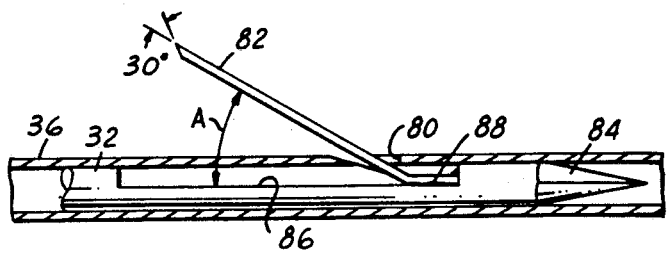
FIG. 12
FIG. 5

LOCALIZATION NEEDLE ASSEMBLY

FIELD OF INVENTION

Localization needles for introduction into and retention in body tissue to identify location for surgical treatment.

BACKGROUND AND OBJECTS OF THE INVENTION

Reference is made to two U.S. patents directed to related subject matter. Markham, U.S. Pat. No. 4,774,948, filed Nov. 24, 1986 and issued Oct. 4, 1988, discloses a barbed stylet slidable in a windowed needle which permits withdrawal of the barb into the needle for retraction. Hawkins et al, U.S. Pat. No. 4,799,495, filed Mar. 20, 1987 and issued Jan. 24, 1989 discloses a similar barbed stylet and tubular needle with a side opening for projection and retraction of a stylet barb. A third and earlier patent, Ellison, U.S. Pat. No. 4,517,965, issued May 21, 1985, shows a tissue retractor needle with barbs which can be cammed out from the needle by an inner stylet.

The present invention has as an object the provision of a barbed stylet within a windowed needle and, in particular, control means for a surgeon to move the barbed stylet to a position of barb retraction and also to a position where the barb is projected out of the needle window into a localization position.

BRIEF DESCRIPTION OF THE INVENTION

Briefly, the invention is directed to a hollow needle hub which anchors the proximal end of a barbed stylet and releasably retains the surrounding needle for movement from a sheathing position for the barb to a position projecting the barb outside the needle. The hub is a one-piece split body resiliently closed and expanded by a surgeon's action to release the cannula or hollow needle for sliding movement to retract or expose the barb.

BRIEF DESCRIPTION OF THE DRAWINGS

DRAWINGS accompany the disclosure and the various views thereof may be briefly described as:

FIG. 1, a plan view of the needle assembly.

FIG. 2, a sectional view on line 2—2 of FIG. 1.

FIG. 3, a view similar to FIG. 2 in an expansion release mode.

FIG. 4, a view illustrating the needle shifted to barb release.

FIG. 5, a sectional view detailing the stylet barb and hollow needle.

FIG. 12, a sectional view on line 12—12 of FIG. 6.

DETAILED DESCRIPTION OF THE INVENTION AND THE MANNER OF AND PROCESS OF USING IT

As viewed in FIGS. 1 to 4, a primary cannula hub 30 mounts the proximal end of an inner cannula member 32 at 34 which is molded into the hub. An outer cannula member 36 has a secondary hub end 40 secured thereto and removably receivable in the cannula hub 30.

Figure 10:
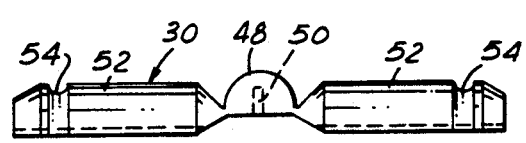
FIGS. 10 and 11, side and plan views of a retainer as molded.
Figure 11:
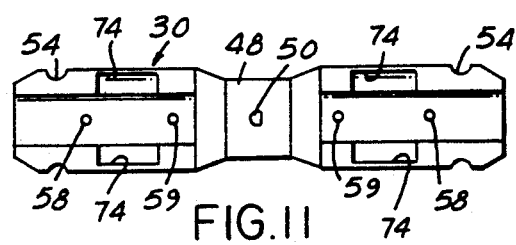

As shown in FIGS. 10 and 11, the cannula hub 30 is formed as a molded part with a center proximal end 48 with a recess 50 for receiving the proximal end of the inner cannula member or stylet 32. Two identical wings 52 are hingedly attached to the center end 48 and each has an outer groove 54 to receive a portion of a flexible band or O-ring. In FIGS. 1 to 4, the wings 52 are shown folded together and retained by a flexible O-ring 56. This O-ring allows the wings 52 to be spread apart as in FIG. 3.

Figure 9:
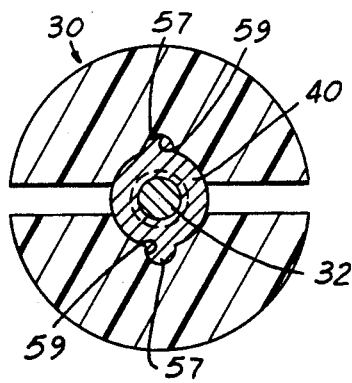
FIG. 9, a sectional view on line 9—9 of FIG. 2.

As shown in FIG. 9, the secondary hub end 40 of the stylet has small knobs or detent projections 57 which fit into opposed recesses 58 or 59 on the inner sides of wings 52 as illustrated in FIG. 11. In FIGS. 1, 2 and 3, the head end 40 of the outer cannula member is shown in the retracted position within the hub 30.

Figure 7:
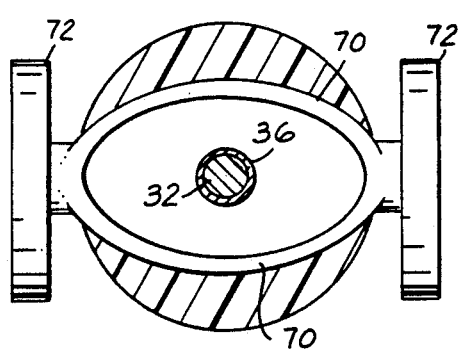
FIG. 7, a sectional view on line 7—7 of FIG. 2.
Figure 8:
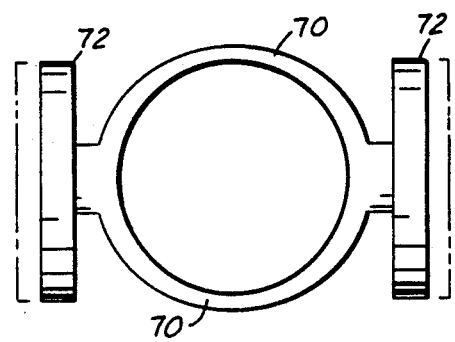
FIG. 8, a view of the expander retainer expanded by side pressure.

An expander for the wings 52 is illustrated in enlarged dimension in FIGS. 7 and 8. It consists of an oval, hollow central element 70 with two pressure plates 72, one on each side, which when pressed together expand the oval 70 to a circular shape as illustrated in FIG. 8. Now with reference to FIG. 2, the oval elements 70 are shown in section in recesses 74 on the inner side of wings 52. The spreader elements 70 are shown in FIG. 2 in the oval collapsed position, while in FIG. 3 the elements 70 are expanded. In the collapsed position the secondary hub end 40 of the outer cannula is retained between the wings 52 at the proximal end of the hub 30. In the expanded position of FIG. 3, the hub end of the outer cannula can be released from its retained position and moved by the operating surgeon to a second retained position near the distal end of the hub 30 as shown in FIG. 4.

The outer cannula 36 with the secondary hub end 40 has a side aperture or window 80 near the distal end. This window preferably tapers toward the proximal end to stabilize the barb 82 as it is projected out of the window 80. The inner needle or stylet 32 has a resilient barb 82 which is normally retained within the outer cannula 36. However, when the outer cannula and secondary hub end 40 are advanced to the position shown in FIG. 4, the barb exits the window 80 and projects as shown in FIGS. 4 and 5. The inner stylet has a sharpened distal end 84 which pilots the combined inner and outer cannula percutaneously into a position to locate a portion of the human body for biopsy, for example. The release of the barb locates the cannulae for X-rays or until a biopsy needle or other surgical device can be introduced in accordance with the particular procedure. As shown in FIG. 12, the barb 82 preferably has a flat cross-section since this provides a greater retention characteristic. The exit angle A of the barb may vary from 23° to 30° depending on the size of the unit and the intended use.

Figure 6:
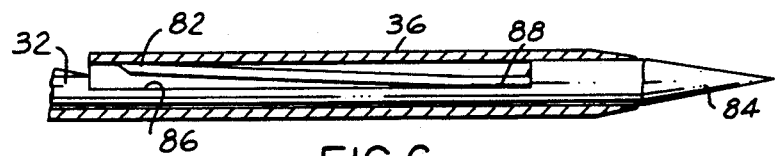
FIG. 6, a sectional view of the sheathed barb.

The retraction of the outer cannula 36 will cam the barb into the outer cannula for removal of the cannulae without damage to the surrounding tissue. The detent recesses 58, 59 serve to orient the cannulae so that the barb 82 is in registry circumferentially with the window 80. The barb 82 can be a separate resilient element welded at its distal end to the surface of a side recess 86 on the inner stylet as at 88 in the enlarged view of FIG. 6.

What is claimed is:

1. In a localization needle assembly of the type utilizing an outer cannula with a barb window adjacent the distal end and an inner needle within the outer cannula having a barb near the distal end to exit from and retract into said window in response to movement of said outer cannula relative to said inner needle, the improvement which comprises:

(a) a primary hub affixed to the proximal end of said inner needle, (b) a secondary hub affixed to the proximal end of said outer cannula to be retained by and shiftable in said primary hub, (c) said primary hub comprising opposed wing elements hinged together by a connection at a proximal end and shaped to provide a central, axially-extending recess, said inner needle having a proximal end secured on said connection between said wings, said secondary hub being positioned in said recess and axially movable between a first secured position in which said barb is located in a retracted position in said outer cannula and a second secured position in which said barb is in an extended position out of said window, said wings being laterally separable from a closed position to release said secondary hub for axial movement within said recess between said first and second positions, (d) resilient means to retain said wings in a closed position, and (e) means between said wings coaxial of said needle manually expandable to separate said wings to release said secondary hub for axial movement.

2. In a localization needle assembly of the type utilizing an outer cannula with a barb window adjacent the distal end and an inner needle within the outer cannula having a barb near the distal end to exit from and retract into said window in response to movement of said outer cannula relative to said inner needle, the improvement which comprises:

(a) a primary hub affixed to the proximal end of said inner needle, (b) a secondary hub affixed to the proximal end of said outer cannula to be retained by and shiftable in said primary hub, (c) said primary hub comprising opposed wing elements having axially spaced means to position and retain said secondary hub axially of said primary hub, said wing elements being movable laterally from a closed position to an open position to release said secondary hub from said means, (d) manually operable means to move said wings laterally of each other to release said secondary hub for axial movement relative to said primary hub, (e) said wings of said primary hub being hinged together at a proximal end in a manner to be spread apart upon actuation of said manually operable means, and (f) resilient means connecting said wings to retain them in closed position but permitting said wings to be spread apart to release the secondary hub for axial movement.

3. In a localization needle assembly of the type utilizing an outer cannula with a barb window adjacent the distal end and an inner needle within the outer cannula having a barb near the distal end to exit from and retract into said window in response to movement of said outer cannula relative to said inner needle, the improvement which comprises:

(a) a primary hub affixed to the proximal end of said inner needle, (b) a secondary hub affixed to the proximal end of said outer cannula to be retained by and shiftable in said primary hub, (c) said primary hub comprising opposed wing elements having axially spaced means to position and retain said secondary hub axially of said primary hub, said wing elements being movable laterally from a closed position to an open position to release said secondary hub from said means, (d) manually operable means to move said wings laterally of each other to release said secondary hub for axial movement relative to said primary hub, (e) said manually operable means comprising a resilient oval loop having opposed sides located between said wings, and (f) pressure means laterally positioned on each side of said wings movable in response to manual pressure to expand said loop and spread said wings apart to release the secondary hub for axial movement.

4. A localization needle assembly as defined in claim 3 in which said pressure means comprises pressure plates disposed at the ends of said oval loop movable to expand said loop.

5. A localization needle assembly as defined in claim 3 in which said oval loop is positioned in opposed openings in said wings axially between said opposed recesses for receiving said secondary hub.

* * * * *